US012144713B2

(12) United States Patent
Glisan et al.

(10) Patent No.: US 12,144,713 B2
(45) Date of Patent: Nov. 19, 2024

(54) MALE INCONTINENCE CONTROL DEVICE AND METHOD OF CONTROLLING MALE INCONTINENCE

(71) Applicant: Assure Medical Group, LLC, Minneapolis, MN (US)

(72) Inventors: Duane L Glisan, Saint Louis Park, MN (US); Ronald C Johansson, Stillwater, MN (US)

(73) Assignee: ASSURE MEDICAL GROUP, LLC, Minneapolis, MN (US)

( * ) Notice: Subject to any disclaimer, the term of this patent is extended or adjusted under 35 U.S.C. 154(b) by 730 days.

(21) Appl. No.: 17/443,695

(22) Filed: Jul. 27, 2021

(65) Prior Publication Data
US 2021/0353398 A1 Nov. 18, 2021

Related U.S. Application Data

(63) Continuation-in-part of application No. 16/755,935, filed as application No. PCT/US2018/060012 on Nov. 9, 2018, now Pat. No. 11,877,919.
(Continued)

(51) Int. Cl.
*A61F 2/00* (2006.01)
(52) U.S. Cl.
CPC .......... *A61F 2/0054* (2013.01); *A61F 2/0004* (2013.01); *A61F 2/0031* (2013.01); *A61F 2210/0057* (2013.01); *A61F 2220/0008* (2013.01); *A61F 2220/0033* (2013.01); *A61F 2230/0006* (2013.01); *A61F 2250/0004* (2013.01); *A61F 2250/001* (2013.01); *A61F 2250/0012* (2013.01); *A61F 2250/0059* (2013.01); *A61F 2250/0069* (2013.01)

(58) Field of Classification Search
CPC ........ A61F 2/0054; A61F 2/0004–0054; A61F 2250/0078; A61F 2250/006–0064
See application file for complete search history.

(56) References Cited

U.S. PATENT DOCUMENTS

| 4,139,007 A | 2/1979 | Diamond |
| 4,539,980 A | 9/1985 | Chaney |

(Continued)

FOREIGN PATENT DOCUMENTS

| CA | 2824958 A1 | 1/2014 |
| CN | 102266256 B | 5/2013 |

(Continued)

OTHER PUBLICATIONS https://web.archive.org/web/20160721050548/http://www.vitalitymedical.com/circlamp-male-incontinence-penis-clamp.html.
https://web.archive.org/web/20160206131116/https://penileclamps.com/dribblestop-penile-clamp.html.

*Primary Examiner* — Rebecca S Preston
(74) *Attorney, Agent, or Firm* — Sherrill Law Offices, PLLC; Michael Sherrill

(57) ABSTRACT

A male incontinence control device with a main elastomeric tubular body, a knob to occlude the urethra, and a feature in the tubular body to accept a spacing device/insert. The length of the spacer will define the minimum internal circumference of the main tube to optimize comfort and performance. There may be multiple sizes of spacers or adjustable spacers, in addition to attachable or adjustable knob embodiments. Removal features are designed to minimize body contact for increased comfort and performance.

21 Claims, 18 Drawing Sheets

Related U.S. Application Data

(60) Provisional application No. 63/057,864, filed on Jul. 28, 2020, provisional application No. 62/684,549, filed on Jun. 13, 2018, provisional application No. 62/583,525, filed on Nov. 9, 2017.

(56) References Cited

U.S. PATENT DOCUMENTS

| | | |
|---|---|---|
| 5,306,227 A | 4/1994 | Osbon et al. |
| 5,842,968 A | 12/1998 | Johnson |
| 5,855,548 A | 1/1999 | Place |
| 6,039,750 A | 3/2000 | Kubalak et al. |
| 6,131,576 A | 10/2000 | Davis |
| 6,138,678 A | 10/2000 | Nilsson |
| 6,234,174 B1 | 5/2001 | Cheng et al. |
| 6,289,895 B1 | 9/2001 | Cheng et al. |
| 6,609,522 B2 | 8/2003 | Cheng et al. |
| 6,827,085 B2 | 12/2004 | Single et al. |
| 6,981,505 B2 | 1/2006 | Krause et al. |
| 7,658,194 B2 | 2/2010 | Anderson et al. |
| 7,658,195 B2 | 2/2010 | Dennis |
| 10,624,728 B2 | 4/2020 | Velez Wiesner |
| 2005/0256365 A1 | 11/2005 | Timm et al. |
| 2006/0081265 A1 | 4/2006 | Warden |
| 2009/0036729 A1 | 2/2009 | Anderson et al. |
| 2013/0053804 A1 | 2/2013 | Sorensen et al. |
| 2014/0041672 A1 | 2/2014 | Garcia Berruezo |
| 2019/0060048 A1 | 2/2019 | Gautieri |
| 2022/0346925 A1* | 11/2022 | Jung .................. A61F 5/44 |

FOREIGN PATENT DOCUMENTS

| | | |
|---|---|---|
| CN | 204468391 U | 7/2015 |
| DE | 10213452 C1 | 7/2003 |
| FR | 2638964 A1 | 5/1990 |
| GB | 2510391 A | 8/2014 |
| KR | 101508140 B1 | 4/2015 |
| WO | 9844852 A1 | 10/1998 |
| WO | 9955251 A1 | 11/1999 |
| WO | 2014027344 A1 | 2/2014 |

* cited by examiner

MALE INCONTINENCE CONTROL DEVICE AND METHOD OF CONTROLLING MALE INCONTINENCE

FIELD OF THE INVENTION

This invention addresses male incontinence, the byproduct of a wide variety of health issues, including aging, prostate surgery or sphincterotomy, medications, kidney disease, and other maladies.

BACKGROUND

Male incontinence is a worldwide problem. It can be the byproduct of a wide variety of health issues, including aging, prostate surgery or sphincterotomy, medications, kidney disease, and others. Incontinence can have a major impact on one's lifestyle. The inability to control urination can affect almost every activity, resulting from fear of consequence or embarrassment.

Nursing homes, with an elderly male population, have a great need for a solution to this problem, which also demands staff attention throughout the day. The impact on active younger men with incontinence may be even greater. Early diagnosis of prostate cancer followed by surgery, for example, can lead to many years or decades of daily lifestyle modifications.

Stopping involuntary urinary flow can be achieved by adequately restricting the urethra, but doing so throughout the day while not causing discomfort or inconvenience has proven to be the challenge. Present art is focused on impeding urinary flow while compromising comfort and convenience. Hard-body mechanisms, including clamps and encirclement devices that wrap around the penis circumference, or otherwise, are unyielding and subject to movement when periodic forces are applied when the user is active. Even normal body movement will place periodic asymmetric pressures on such devices, thereby imparting forces which may cause a displacement and/or discomfort.

Hardbody design requires positioning forward from the penis base, thereby subjecting the unit to increased body contact and potential movement when the user is active, and reduced performance requiring increased perimeter pressures. Forward positioning allows urine to advance in the urethra to the constriction point, which is outside the body. When changing positions, such as when sitting down, urethral pressures build, thereby forcing leakage through the control device. Avoiding such episodes often requires tighter perimeter pressures to increase constrictive urethral pressure, thereby increasing discomfort with extended use. With a rigid construction, the present art fails to adjust to increased blood flow or vascular pressure, causing discomfort at times when being worn.

The present art requires removal, adjustment, or repositioning prior to regular urinations. After urination, the process is reversed. Such demands do not always suit the circumstances when the need for urination arises. Convenience is not a medical term, but to many users it can also be a fundamental requirement in addition to comfort, effective urinary control, and limited impact on blood circulation.

Accordingly, a need exists for a male incontinence control device that is convenient to use and performs well without discomfort or required management throughout the day prior to, during, or after urination.

SUMMARY OF THE INVENTION

The invention is directed to a male incontinence control device and related methods of using the device.

The invention features a flexible elastomeric-sleeve body with an incorporated protrusion (knob) for applying pressure to the urethra for male incontinence control. Its objective is to provide all-day comfort, convenience in use, and sufficient performance to manage involuntary leakage, unlike the hard-body alternatives. The material and configuration allow it to be positioned close to the base of the penis for maximum performance. Its adjustability features produce the least amount of tension for the desired performance.

The invention provides performance in impeding urinary leakage, is comfortable for extended wear, convenient to use and offers the ability to increase and decrease pressure on the urethra to suit the needs of the user, while minimizing the impact on blood circulation. Given the forward bias of the lower removal feature/loop, it may be worn close to the penis base producing better performance by reducing urine in the urethral tract external to the body, in addition to minimal body contact that would otherwise tend to displace it. Under certain conditions with increased blood flow, the flexible-unit body does not cause discomfort, unlike the rigid-body alternatives. The flexible-body characteristic allows the user to urinate through the device constriction point, without requiring adjustment or removal before urination, by slightly increasing pelvic floor muscle pressure. Alternatively, the user can apply a small vertical tension (expansion) on the two removal loops to reduce the pressure on the urethra for urinating. Note that this does not result in the device changing position on the penis.

The flexible body of the invention addresses the critical need for comfort throughout the day, convenience, in that it requires little management, and sufficient performance with its minimal impact on lifestyle. The present invention, with its flexible-body construction designed to be worn at the base of the penis at minimal tension, and adjustability, while allowing the user to urinate through it without manipulation, is an advance beyond the present art of hard-body construction.

In a first embodiment, the male incontinence control device is a male incontinence control device that includes (a) a single-piece continuous loop of an elastic compression band defining a lumen, the elastic compression band configured and arranged to securely encircle a flaccid penis without inflicting penile ischemia, and (b) an inwardly projecting bump on the elastic compression band configured and arranged for pressing against and constricting the urethra of a wearer.

In a second embodiment, the male incontinence control device is (a) a continuous looped band of material defining a lumen wherein the band has an integrated first elastic length and a second inelastic length, and is configured and arranged to securely encircle a flaccid penis without inflicting penile ischemia, and an inwardly projecting bump on the band configured and arranged for pressing against and restricting the urethra of a wearer.

In a third embodiment, the male incontinence control device provides multiple means by which size/tension may be modified to accommodate the varying needs of individuals of different stature. Sizing inserts (spacers) incorporated into an elastomeric unit/sleeve may be of various shapes and sizes, including fixed sizes, as well as adjustable art, that allows for expansion or reduction of the main body's circumference. Additionally, an integrated protrusion/knob positioned to occlude the urethra may be modified in size and shape or by the use of inserts or with replaceable knobs.

The third embodiment is directed to a male incontinence control device, which includes an elastomeric sleeve/band with a urethra compression feature and a spacing insert/mechanism to modify the unit dimension and urethral pressure. Urethral pressure may also be adjusted via the integrated protrusion disposed at the lower interior of the main sleeve body that can be modified by the use of caps, inserts or other means to increase or decrease the height, length, width and/or hardness of the protrusion.

The lumen of the male incontinence control device preferably has an elliptic cross-section with a major axis centered through a top and bottom portion of the elastic compression band and a minor axis centered through side portions of the elastic compression band, and the volumetric center of the bump is essentially aligned with the minor axis.

The device preferably includes diametrically opposed first and second removal loops extending radially outward from the elastic compression band in alignment with the minor axis of the lumen, with the removal loops configured and arranged to accommodate passage of at least one fingertip through each removal loop to facilitate manual outward radial stretching of the elastic compression band.

The device is operable for controlling male incontinence, by (i) manually radially stretching the continuous elastic compression band so as to enlarge the lumen, (ii) inserting the penis of a male in need of incontinence control through the enlarged lumen with the bump on the device positioned proximate the underside of the penis, and (iii) releasing the band whereby the band contracts around the shaft of the penis, and the bump presses against and restricts the urethra.

A male wearing the device can urinate while wearing the device by consciously initiating voiding of his bladder without adjusting or removing the device, whereby (i) the bladder contracts, (ii) the bladder outlet relaxes, and (iii) the flow of urine within the urethra exerts a pressure sufficient to overcome the pressure exerted upon the urethra by the bump on the device so as to permit micturition.

The device, when equipped with removal loops, can be removed from operable engagement with a penis by (i) inserting at least one finger tip from a first hand into the first removal loop, and inserting at least one finger tip from a second hand into the second removal loop, (ii) manually stretching the elastic compression band so as to enlarge the lumen by pulling the loops away from one another, and (iii) sliding the manually stretched elastic compression band off the penis.

The device, when equipped with removal loops, can also be removed from operable engagement with a penis by (i) inserting at least a first and a second finger tip from a first hand into the first removal loop, and inserting at least a first and a second finger tip from a second hand into the second removal loop, (ii) manually radially stretching the elastic compression band so as to enlarge the lumen by both pulling the loops away from one another and expanding the first and second finger tips in each removal loop away from one another, and (iii) sliding the manually stretched elastic compression band off the penis.

An object of this invention is to provide a male incontinence control device that can be worn in comfort day and night, constructed of elastomeric material or compounds including, but not limited to, Silicone rubber, natural Rubber, Thermoplastic Elastomers (TPE), Thermoplastic Rubbers (TPR) and similar elastomer and elastomeric materials.

Another object of this invention is to provide men with a control device that is comfortable to wear for extended periods, convenient to use, and affords protection against involuntary urinary leakage.

Another object of this invention is to provide an incontinence control device of a flexible sleeve body of elastomeric material.

Another object of this invention is to provide a control device that provides day and night incontinence management for men.

Another object of this invention is to provide a control device that reduces the need for diapers and pads for incontinent men.

Another object of this invention is to provide men with a control device with removal features that have a forward bias away from the user, allowing for positioning at the base of the penis for improved performance and comfort.

Another object of this invention is to provide men with a control device with few activity restrictions when in use.

Another object of this invention is to provide men with a control device with upper and lower removal features/loops that, when put in tension in opposite directions, lower the constrictive pressure on the urethra, allowing a complete voiding of urine.

Another object of this invention is to provide a male incontinence control device that allows normal blood circulation to the penis while being worn for extended periods of time.

Another object of this invention is to provide a male incontinence control device that significantly impedes involuntary urinary flow.

Another object of this invention is to provide a male incontinence control device that typically requires no management or adjustment before, during, or after urination.

Another object of this invention is to provide a male incontinence control device that minimizes skin irritations.

Another object of this invention is to provide a male incontinence control device that is adjustable in tension by removal of material.

Another object of this invention is to provide a male incontinence control device that can be worn while sleeping.

Another object of this invention is to provide a male incontinence control device that does not require adjustment from a day's beginning to end, after the initial adjustment/fitting.

Another object of this invention is to provide a male incontinence control device that is easy to don and doff.

Another object of this invention is to provide a male incontinence control device that may employ an integrated protrusion disposed at the lower interior of the main sleeve body that can be modified in size or hardness by the use of inserts or caps to increase or decrease the height, length, width and/or hardness of the protrusion.

Another object of this invention is to provide a male incontinence control device constructed of a flexible body that allows urine to flow through the point of constriction, when urinary pressures within the urethra are increased, without prior adjustment or removal of the device.

Another object of this invention is to provide a male incontinence control device that additionally improves performance in impeding involuntary leakage when sitting.

Another object of this invention is to provide a male incontinence control device that may employ an integrated protrusion disposed at the lower interior of the main sleeve body which contains a harder insert molded core element to provide a firmer protrusion.

Another object of this invention is to provide an incontinence control device with adjustable dimensions/tension for controlling male incontinence.

Another object of this invention is to provide an incontinence control device with a spacer device that is interchangeable which will limit the perimeter pressure on the penis.

Another object of this invention is to provide an incontinence control device with a spacing device which may be of varying lengths and configurations, fixed or adjustable in length.

Other objects and advantages of the various embodiments of the present invention will become obvious to the reader and it is intended that these objects and advantages are within the scope of the present invention To the accomplishment of the above and related objects, this invention may be embodied in the form illustrated in the accompanying drawings, attention being called to the fact, however, that the drawings are illustrative only, and that changes may be made in the specific construction illustrated and described within the scope of this application.

BRIEF DESCRIPTION OF THE DRAWINGS

Example embodiments will become more fully understood from the detailed description given herein below and the accompanying drawings, wherein like elements are represented by like reference characters, which are given by way of illustration only and thus are not limitative of the example embodiments herein.

DETAILED DESCRIPTION OF A PREFERRED EMBODIMENT

Definitions

Figure 1:
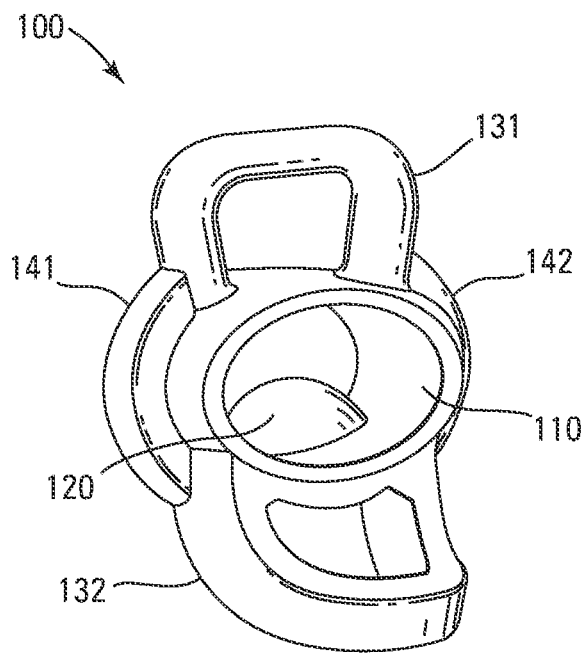
FIG. 1 is a perspective view of one embodiment of the invention.

As utilized herein, including the claims, the phrase "essentially aligned", when used in reference to the position of the volumetric center of the bump relative to the minor axis of the lumen, means less than about 2 mm distance from the minor axis along a 90° straight-line.

As utilized herein, including the claims, the phrase "low modulus" means a Young's Modulus of 5 to 30 psi.

As utilized herein, including the claims, the phrase "generally spherical object" means an object having no sharp edges or corners, such as a sphere, a torus, an ellipsoid, an egg-shaped object, a pear-shaped object, a 100-sided polyhedron, etc.

| Nomenclature Table | |
|---|---|
| REF. NO. | NAME |
| 100 | Male Incontinence Control Device |
| 110 | Elastic Compression Band, Elastic Cylindrical Annulus, or Sleeve |
| 110a | Top Portion of Elastic Compression Band |
| 110b | Bottom Portion of Elastic Compression Band |
| 110s | Side Portions of Elastic Compression Band |
| 119 | Lumen Through the Elastic Compression Band or Void |
| 119α | Axial Directions of Lumen |
| 119α$_1$ | Forward Axial Direction of Lumen |

-continued

Nomenclature Table

| REF. NO. | NAME |
|---|---|
| $119\alpha_2$ | Rearward Axial Direction of Lumen |
| $119\beta$ | Radial Directions of Lumen |
| $119x$ | Length of Lumen |
| 120 | Bump or Protrusion |
| 130 | Removal Appliances (Loops) or Gripping Appendages |
| 131 | First Removal Appliance |
| 132 | Second Removal Appliance |
| 140 | Radial Wings |
| 141 | First Radial Wing |
| 142 | Second Radial Wing |
| 150 | Axial Wings |
| $151_1$ | First Forward Axial Wing |
| $152_1$ | Second Forward Axial Wing |
| $151_2$ | First Rearward Axial Wing |
| $152_2$ | Second Rearward Axial Wing |
| 200 | Insert |
| 300 | Post for Detachable Mounting of Bump |
| 410 | Inelastic Length of Band |
| 420 | Elastic Length of Band |
| 430 | Connection Mechanism |
| P | Penis |
| $P_1$ | Shaft of Penis |
| $P_2$ | Underside of Penis |
| S | Scrotum |
| U | Urethra |
| W | Wearer |
| 600 | Male Incontinence Control Device |
| 610 | Elastomeric Body or Elastomeric Member |
| 611 | Tubular Main Body, Tubular Elastomeric Primary Band, or Sleeve |
| 612 | Upper Loop |
| 613 | Lower Loop |
| 614 | Internal Bump or Knob |
| 615 | Spacer Insert Holding Strap, Elastomeric Secondary Band or Member for Receiving Spacer |
| 616 | Spacer Connecting Post or Central Attachment Post |
| 617 | Gusset |
| 620 | Spacer or Spacing Device |
| 621 | Main Body Arc |
| 622 | Front Stop |
| 623 | Rear Keeper Disks |
| 624 | Center Slot or Niche |
| 630 | Adjustable Spacer Outer Arc |
| 631 | Main Body Arc |
| 632 | Front Stop Outer Arc |
| 633 | Dovetail Female Slots in Outer Arc |
| 640 | Adjustable Spacer Inner Arc |
| 641 | Main Body Arc |
| 642 | Front Stop Inner Arc |
| 643 | Dovetail Male Parts in Inner Arc |
| 650 | Adjustable Spacer Assembled Narrow |
| 651 | Main Body Arc |
| 660 | Adjustable Spacer Assembled Wide |
| 670 | Elastomeric Body with Hole for Knob Insert |
| 671 | Tubular Main Body |
| 672 | Knob with Hole for Insert |
| 673 | Center Ridge |
| 680 | Knob Inserts or Objects |
| 681 | Small Knob Insert |
| 682 | Medium Knob Insert |
| 683 | Large Knob Insert |
| 684 | Insert Groves |
| 690 | Elastomeric Body with a Knob Insert Assembled |
| 691 | Tubular Main Body |
| 692 | Knob with Hole |
| 693 | Knob Insert |

First Aspect

Construction

The male incontinence control device 100 is designed with comfort being one objective. It is constructed with a low modulus of elasticity elastomer material that allows the user to remain unaware of its presence throughout the day, when properly sized.

The male incontinence control device 100 is preferably configured and arranged not to completely impede urinary flow, but to greatly reduce involuntary urine flow while remaining comfortable to wear without inconvenience. In its preferred configuration and arrangement, persons wearing the device 100 may experience minor leakage for a variety of reasons throughout the day. Sudden increases in intravesical pressure may be generated when lifting a heavy weight, pressures from a full bladder, involuntary relaxation of the sphincter, or simply coughing or sneezing, in addition to urge incontinence.

The profile of the male incontinence control device 100 is modest in each dimension, which minimizes body contact and any tendency for movement. Comfort is directly related to the degree of constriction, which affects blood flow, and friction. Friction is created by contact pressures and movement between the device 100 and the surface of the skin.

Referring generally to FIGS. 1-5, according to the principles of the invention, the main body construction of the male incontinence control device 100 is a generally elastic cylindrical annulus, referred to herein as a sleeve or continuous loop elastic compression band 110, and an integrated protrusion, referred to herein as a bump 120, on the interior wall. The band 110 and bump 120 are preferably formed as a single-piece. Attached gripping appendages, referred to herein as removal appliances or removal loops 130, are preferably provided.

Figure 2:
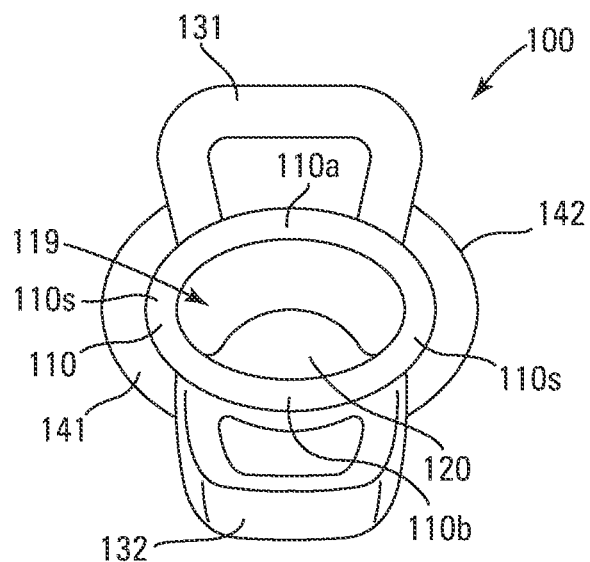
FIG. 2 is a front view of the invention depicted in FIG. 1.
Figure 3:
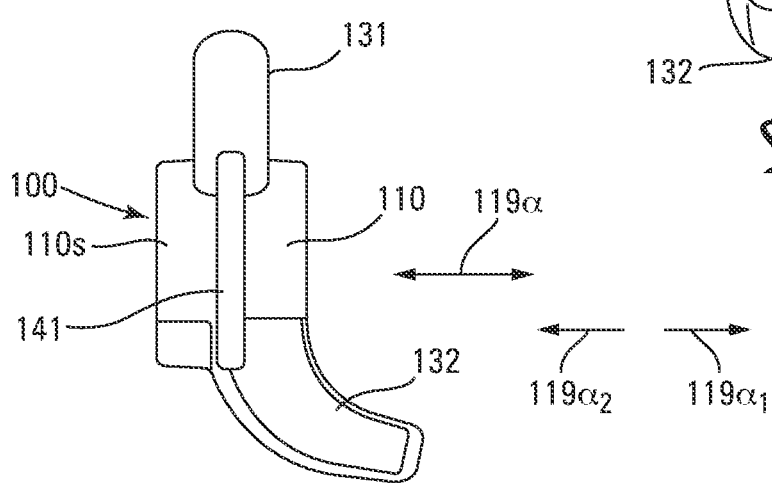
FIG. 3 is a side view of the invention depicted in FIG. 1.
Figure 4:
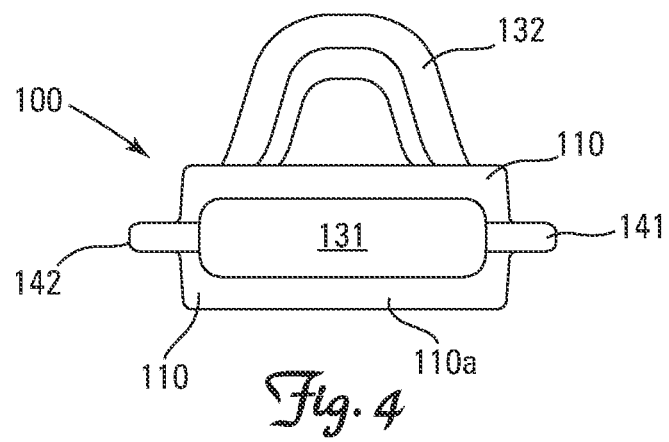
FIG. 4 is a top view of the invention depicted in FIG. 1.

Referring generally to FIGS. 1 and 2, the outer surface and the inner surface of the sleeve 110 defines the majority of the body of the sleeve 110. The inner face of the sleeve 110 bounds a cylindrical void, referred to herein as a lumen 119, which receives the penis P in the applied condition. The inner circumference of the sleeve 110 corresponds to, but is less than that of the flaccid penis P so as to securely encircle the flaccid penis P without inflicting penile ischemia.

An elastic compression band 110 having a thickness of 1 to 5 mm and defining a lumen 119 having an axial length of 1 to 2 cm is generally effective for providing a combination of comfort and superior performance.

The continuous loop elastic compression band 110 can be conveniently demarcated for purposes of describing the relative location of features and components on the continuous loop elastic compression band 110 as having a top portion 110a, a bottom portion 110b, and side portions 110s. The lumen 119 defines an axial direction $119\alpha$ and radial directions $119\beta$. The axial direction $119\alpha$ has a forward axial direction $119\alpha_1$ and a rearward axial direction $119\alpha_2$. The lumen 119 has an axial length $119x$.

The lumen 119 can have an elliptic cross-section with a major axis centered through the top 110a and bottom 110b portions of the elastic compression band 110 and a minor axis centered through the side portions 110s of the elastic compression band 110.

The continuous loop elastic compression band 110 provides a relatively large cylindrical surface area in contact with the surface of the penis P relative to that of the small integrated protrusion 120 deposed at the lower 110b interior of the main sleeve body 110 which concentrates upward pressure on the urethra U located on the underside $P_2$ of the penis P to impede urinary flow. This spreads constriction forces over a larger area around the perimeter of the penis P, relative to other configurations such as a cylindrical shaped (cross-section) loop, thereby allowing for normal blood flow and avoiding penile ischemia by minimizing constriction pressure. The distributed constriction force results in low pressures on the grouping of veins, arteries, and nerves commonly referred to as the neurovascular bundle, which ensures normal circulation and comfort.

The continuous cylindrical sleeve 110 is composed of a rubber, silicone or other elastomer commonly known to the trade. The sleeve 110 preferably has (i) a shore durometer of 5A to 30A, (ii) a low modulus of elasticity (i.e., a Young's Modulus of 5 to 30 psi and preferably 5 to 20 psi), and (iii) an ultimate elongation of at least 100%. A durometer of less than about 5A tends to provide insufficient constriction force when used, while a durometer of greater than about 30A tends to be excessively difficult to stretch when donning and doffing the device 100. Similarly a modulus of elasticity of less than about 5 psi tends to provide insufficient constriction force when used, while a modulus of elasticity of greater than about 30 psi tends to be excessively difficult to stretch when donning and doffing the device 100. Finally, an ultimate elongation of less than 100% tends to be excessively difficult to stretch a sufficient amount when donning and doffing the device 100.

Figure 5:
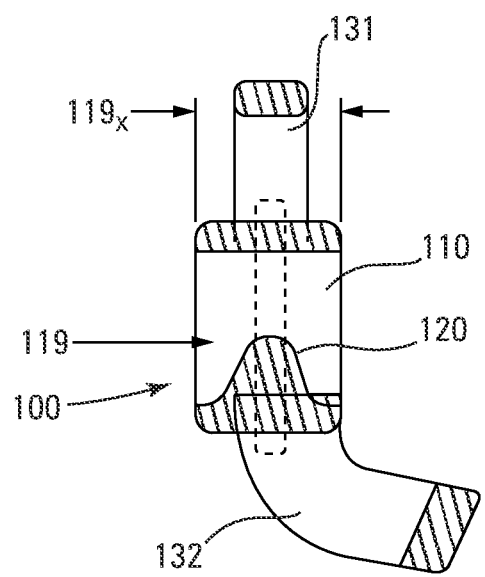
FIG. 5 is a cross-sectional view of the invention depicted in FIG. 2 taken along line 5-5.

Referring generally to FIGS. 1, 2 and 5, an integrated protrusion 120 is deposed on the inner wall of the continuous cylindrical sleeve 110 at the bottom 110b, extending radially inwardly and upward when in the applied condition for pressing against and constricting the urethra U of a wearer W.

A bump 120 which radially extends 5 to 15 mm into the lumen 119 is generally effective for providing a combination of comfort and superior performance.

In the preferred embodiment, the bump 120 has an uppermost convex surface, and is integrally attached to the lower 110b interior of the inner wall of the sleeve 110. The bump 120 preferably projects radially inward 119B directly towards the center of the lumen 199. Other embodiments may include, but are not limited to, protrusions composed of caps or inserts, which may not be an integral component to the sleeve 110 itself.

Referring generally to FIGS. 8-11, the bump 120 may be of solid elastomer material or may incorporate a variety of insert/snap-on components 200 of different size, shape and/or hardness (durometer) for insertion into a void within the bump 120 to increase hardness, adding to upward pressure on the urethra U. Alternatively, bumps 120 of different size, shape and/or hardness (durometer) may selectively attachable to the continuous cylindrical sleeve 110 via an inwardly projecting post 300 on the sleeve 110 to adjust upward pressure on the urethra U.

Referring generally to FIGS. 2 and 5, when the lumen 119 defined by the continuous loop elastic compression band 110 has an elliptic cross-section, the volumetric center of the bump 120 is preferably essentially aligned with the minor axis of the lumen 119.

Referring generally to FIGS. 1-5, the male incontinence control device 100 may have gripping appendages, referred to herein as removal appliances or removal loops 130 in the preferred embodiment, integrally attached to the continuous cylindrical sleeve 110. A first removal appliance 131 is deposed at the upper perimeter outer wall 110a extending radially outward, and an opposed second removal appliance 132 is deposed at the lower perimeter outer wall 110b. The lower removal appliance 132 may be attached at a forward $119\alpha_1$ angle to the main body 110 and a forward 11901 angle when in the applied condition. This forward $119\alpha_1$ bias from a horizontal or vertical axis, which is directed away from the body, can reduce contact with skin around the penis P.

The removal appliances 130 may be of any shape capable of allowing the continuous cylindrical sleeve 110 to be manipulated as necessary with ease and efficiency. Elderly men or those with impaired vision or dexterity should have little difficulty placing the device 100 into the proper position, particularly when the removal appliances 130 are formed as loops.

Referring generally to FIGS. 1-5, the removal appliances 130 are preferably configured and arranged for manual fingertip engagement to facilitate manual outward radial stretching of the elastic compression band 110. For ease of use, the removal appliances 130 are preferably diametrically opposed removal loops configured and arranged to accommodate passage of at least one fingertip and preferably two fingertips through each removal loop to facilitate manual outward radial stretching of the elastic compression band 110. When the lumen 119 defined by the continuous loop elastic compression band 110 has an elliptic cross-section, the removal appliances preferably extend radially outward from the elastic compression band in alignment with the minor axis of the lumen 119.

Referring generally to FIGS. 1, 3, 5 and 12, the removal appliance 130 closest to the bump 120 will typically contact and rub against the scrotum S during normal usage. In order to minimize any discomfort this removal appliances 130 can be angled axially forward $119\alpha_1$ from the elastic compression band 110. To further minimize any discomfort this scrotum-engaging removal appliances 130 preferably curves axially forward $119\alpha_1$ from the elastic compression band 110 at a radius of curvature of between about 1 to 2 cm, with the understanding that the curvature may be a compound curve with or without some linear segments which approximates a radius of curvature of between about 1 to 2 cm.

The gripping appendages 130 of other embodiments may be of another shape, size, material and position, lending to aesthetic or functional qualities.

Referring generally to FIGS. 1-4, the male incontinence control device 100 may include opposed trimmable appendages, referred to herein as radial wings 140 extending radially outward from the continuous loop elastic compression band 110.

The radial wings 140 preferably have an axial $119\alpha$ length of less than ½ that of the elastic compression band 110 so as to provide a limited area of increased radial thickness of elastic material to the side portions 110s of the elastic compression band 110.

In a preferred embodiment, the opposed removable radial wings 140 project laterally (i.e., radially) from the side portions 110s of the sleeve 110 outer wall a radial distance of between 2 and 10 mm when in the applied condition, with a first radial wing 141 projecting from a first side portion and a second radial wing 142 projecting from a second side portion. The radial wings 140 are preferably constructed of the same soft elastic material as the sleeve 110, sufficient in volume to increase sleeve 110 tension when in the applied condition and therefore, when removed or reduced, will decrease tension to adjust for varying user needs.

To adjust for proper tension and to ensure normal blood circulation when in the applied condition, the opposing radial wings 140 may be trimmed using common scissors to incrementally remove material.

Figure 6:
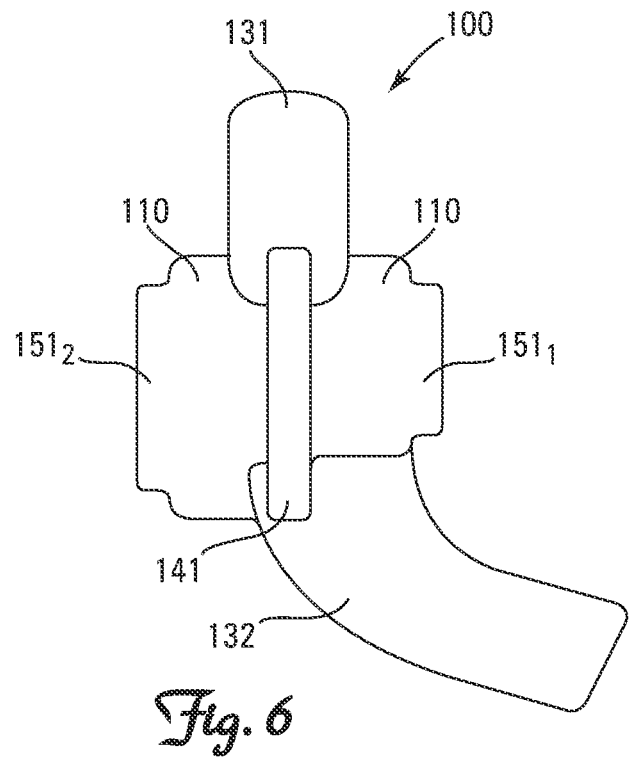
FIG. 6 is a side view of the invention depicted in FIG. 1 equipped with axial wings.
Figure 7:
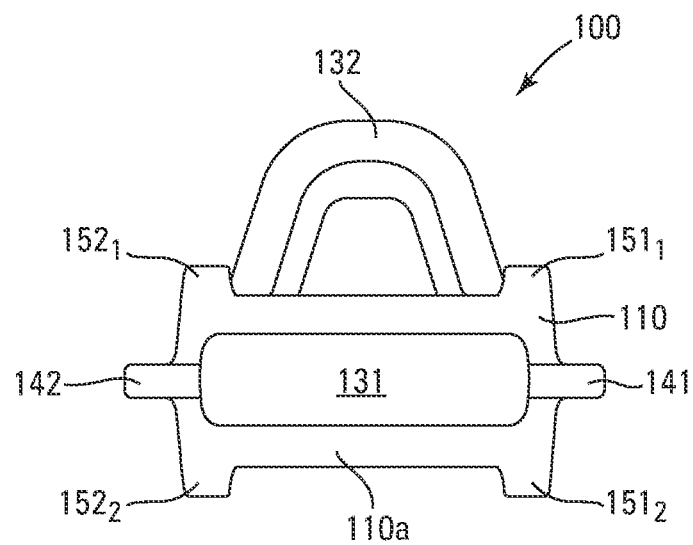
FIG. 7 is a top view of the invention depicted in FIG. 6.
Figure 8:
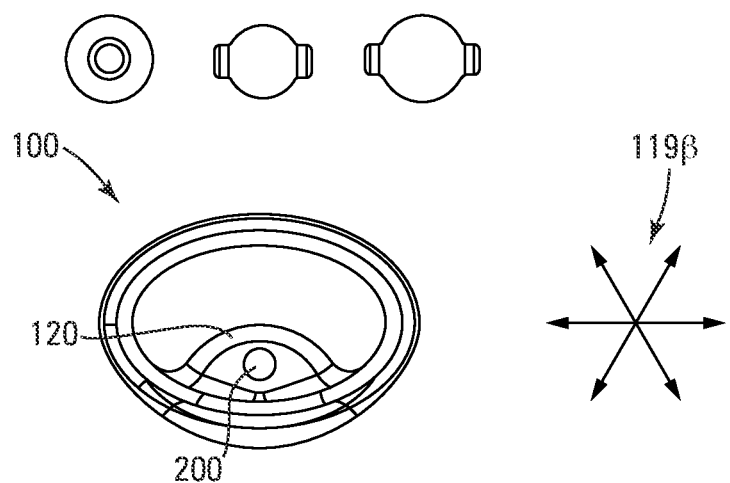
FIG. 8 is a front view of a second embodiment of the invention and multiple spherical objects configured and arranged for selective insertion into the bump.
Figure 9:
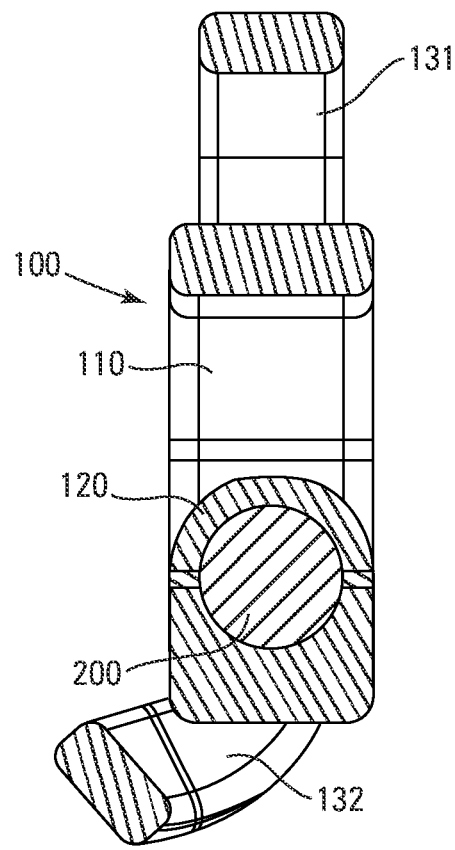
FIG. 9 is a cross-sectional view of a second embodiment of the invention equipped with a generally spherical object replaceably captured within the bump.
Figure 10:
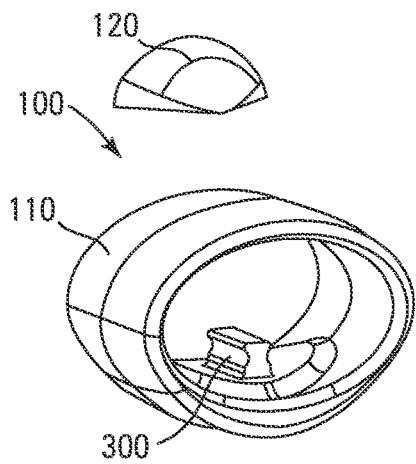
FIG. 10 is an exploded perspective view of a third embodiment of the invention having a detachable and replaceable bump.
Figure 11:
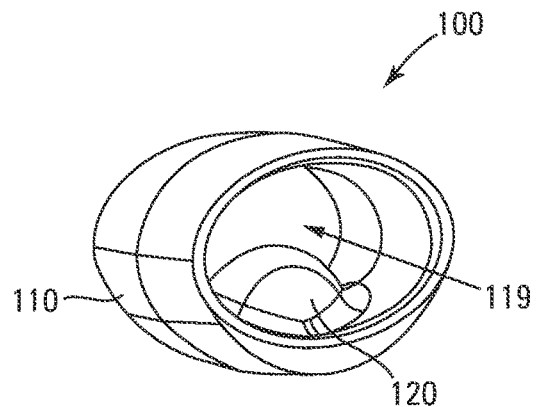
FIG. 11 is a perspective view of the third embodiment of the invention depicted in FIG. 10 with the bump attached to the band.
Figure 12:
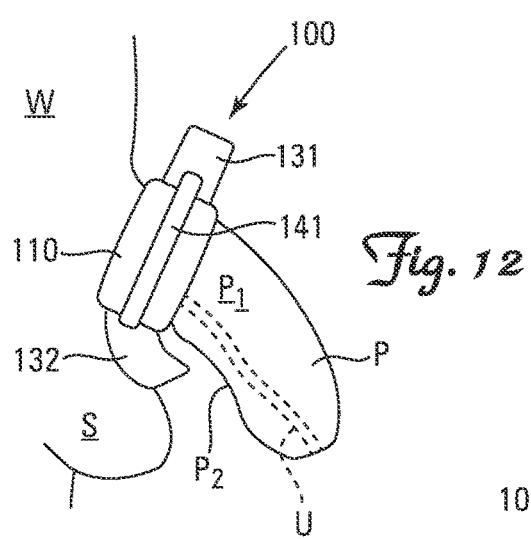
FIG. 12 is a side view of the invention depicted in FIGS. 1-5 worn by an individual.

Referring generally to FIGS. 6 and 7, the male incontinence control device 100 may, in addition to or instead of the radial wings 140, include forward $119\alpha_1$ and/or rearward $119\alpha_2$ extending pairs of laterally opposed trimmable appendages, referred to herein as axial wings 150 extending from the continuous loop elastic compression band 110.

The removable axial wings 150 project longitudinally (i.e., axially) forward $119\alpha_1$ and/or rearward $119\alpha_2$ from the side portions 110s of the sleeve 110 an axial distance of between 2 and 10 mm when in the applied condition. A first forward axial wing $151_1$ projects from a first side portion 110s and a second forward axial wing $152_1$ projects from a second side portion 110s. In similar fashion, a first rearward axial wing $151_2$ projects from a first side portion 110s and a second rearward axial wing $152_2$ projects from a second side portion 110s. The axial wings 150, as with the radial wings 140 are preferably constructed of the same soft elastic material as the sleeve 110, sufficient in volume to increase sleeve 110 tension when in the applied condition and therefore, when removed or reduced, will decrease tension to adjust for varying user needs.

To adjust for proper tension and to ensure normal blood circulation when in the applied condition, the axial wings 150 may, as with the radial wings 140, be trimmed using common scissors to incrementally remove material.

Other embodiments may include removable features of another shape or size sufficient to modify functional qualities.

The male incontinence control device 100 (i.e., the continuous loop elastic compression band 110, bump 120, removal appliances 130 and radial wings 140) may be formed as a unitary molding of the elastomer material, employing injection, transfer, or compression molding processes.

Figure 13:
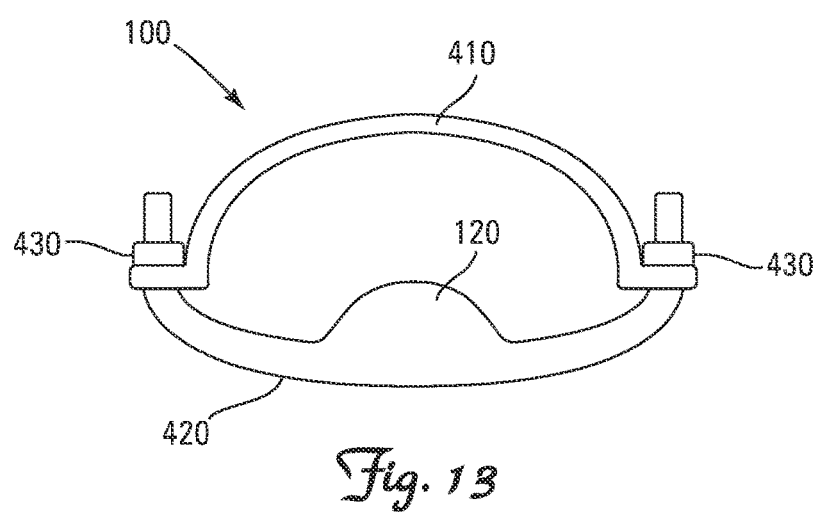
FIG. 13 is a front view of a fourth embodiment of the invention.
Figure 14:
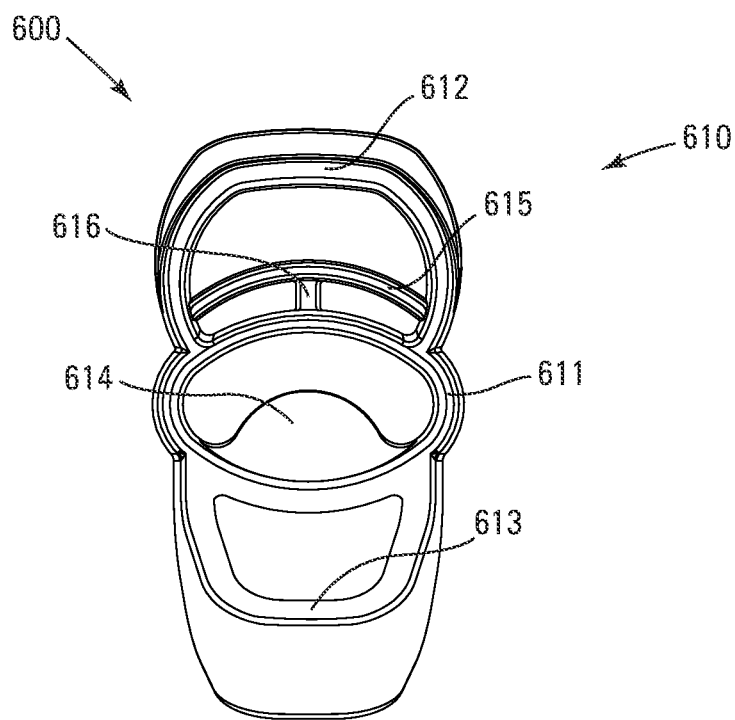
FIG. 14 is a front view of the main body of a fifth embodiment of the invention without a spacing insert (spacer) installed.
Figure 15:
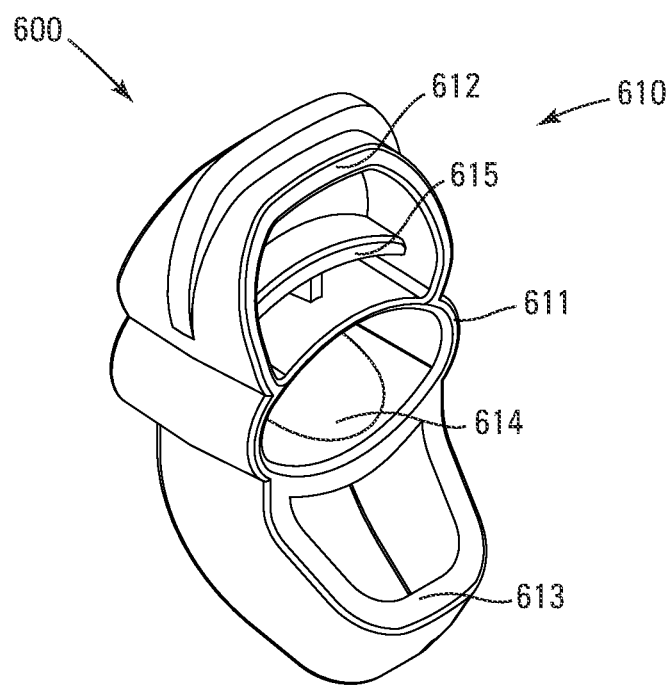
FIG. 15 is an upper perspective view of the invention depicted in FIG. 14 without a spacer installed.
Figure 16:
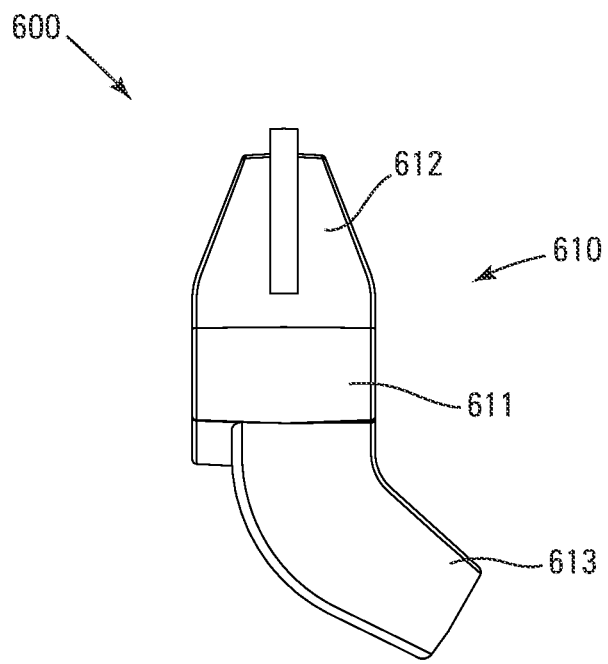
FIG. 16 is a side view of the main body of the invention depicted in FIG. 14.
Figure 17:
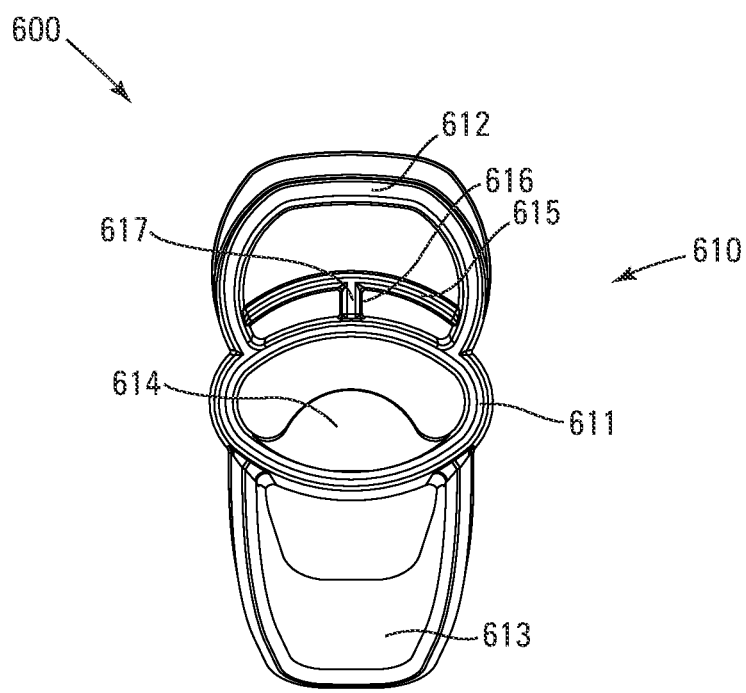
FIG. 17 is a rear view of the invention depicted in FIG. 14 without a spacer installed.
Figure 18:
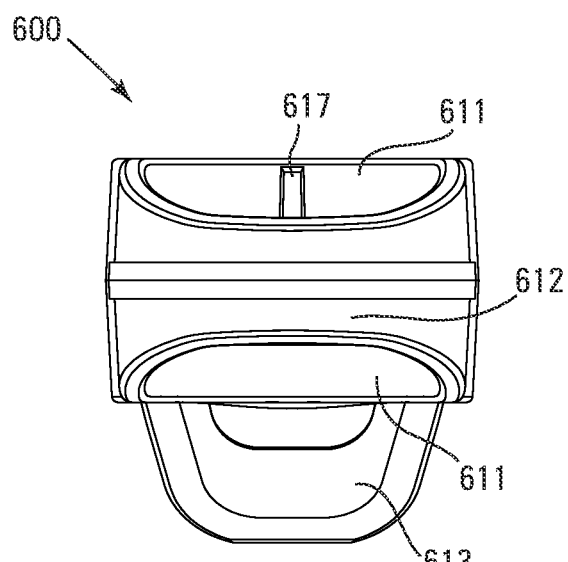
FIG. 18 is a top view of the main body of the invention depicted in FIG. 14.
Figure 19:
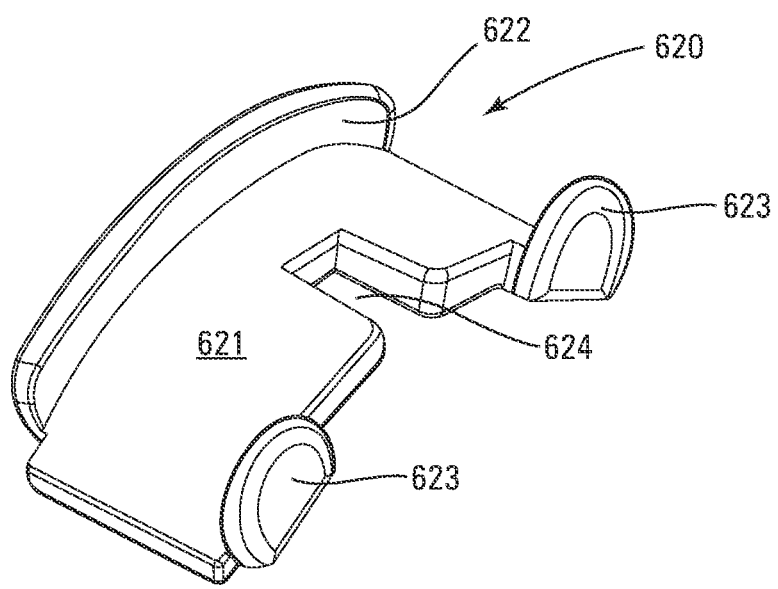
FIG. 19 is an upper perspective view of one version of a spacer component suitable for use with the invention depicted in FIG. 14.
Figure 20:
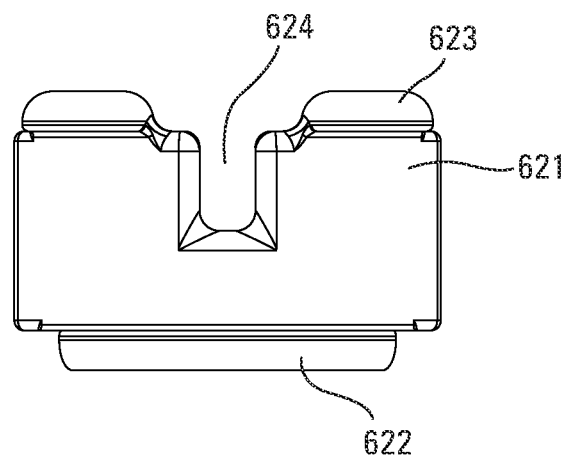
FIG. 20 is a top view of the spacer depicted in FIG. 19.
Figure 21:
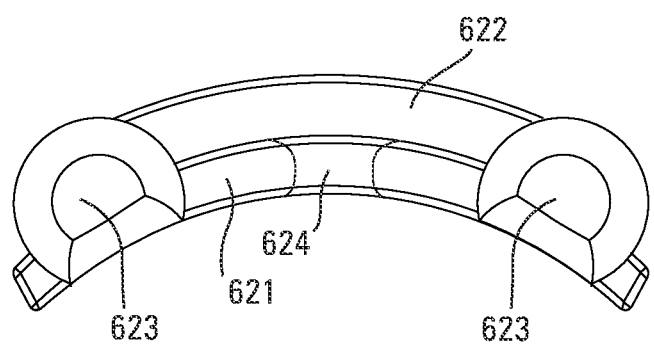
FIG. 21 is a rear view of the spacer depicted in FIG. 19.
Figure 22:
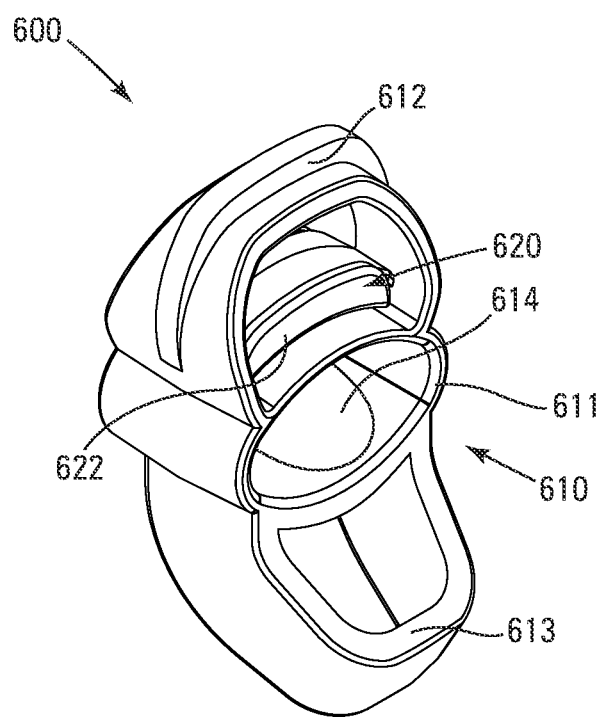
FIG. 22 is an upper perspective view of the spacer depicted in FIG. 19 inserted into the main body of the invention depicted in FIG. 14.
Figure 23:
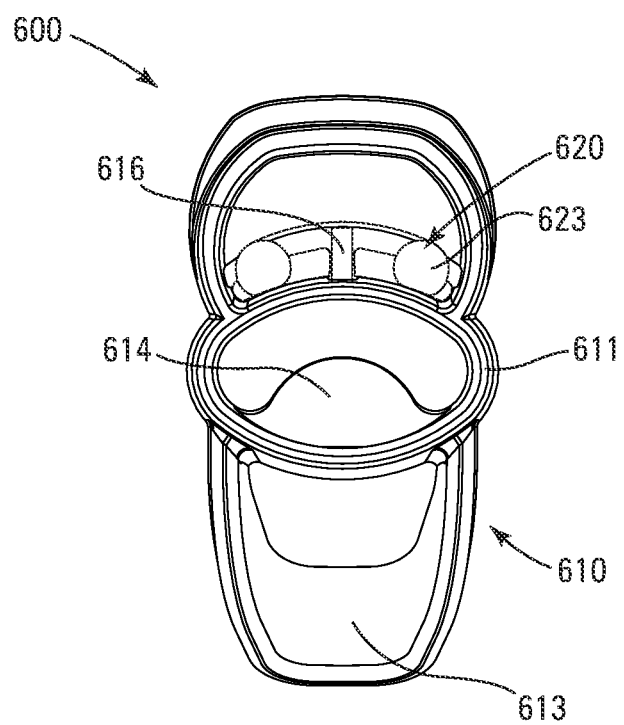
FIG. 23 is a rear view of the assembly depicted in FIG. 22.
Figure 24:
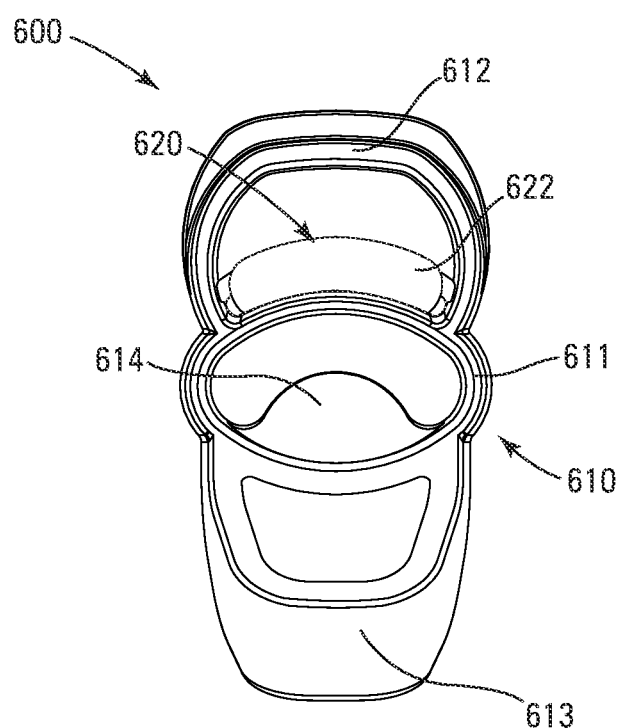
FIG. 24 is a front view of the assembly depicted in FIG. 22.
Figure 25:
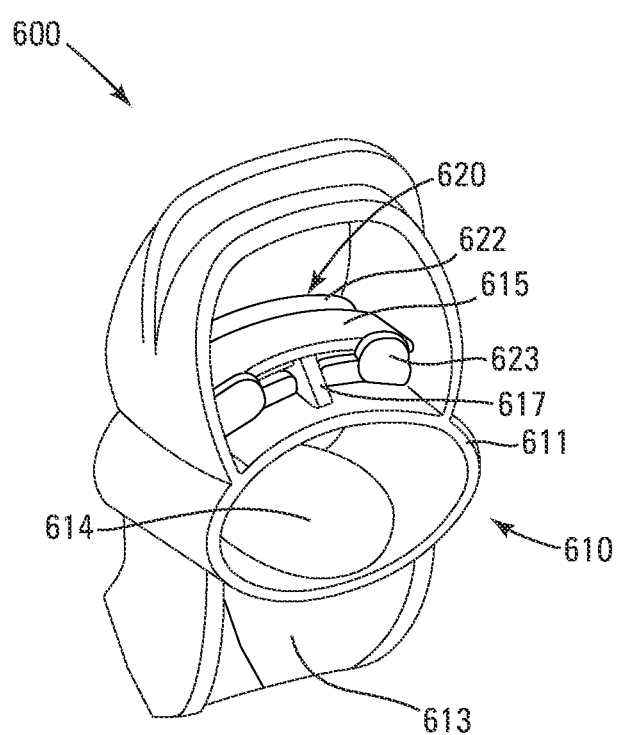
FIG. 25 is an upper perspective rear view of the assembly depicted in FIG. 22.
Figure 26:
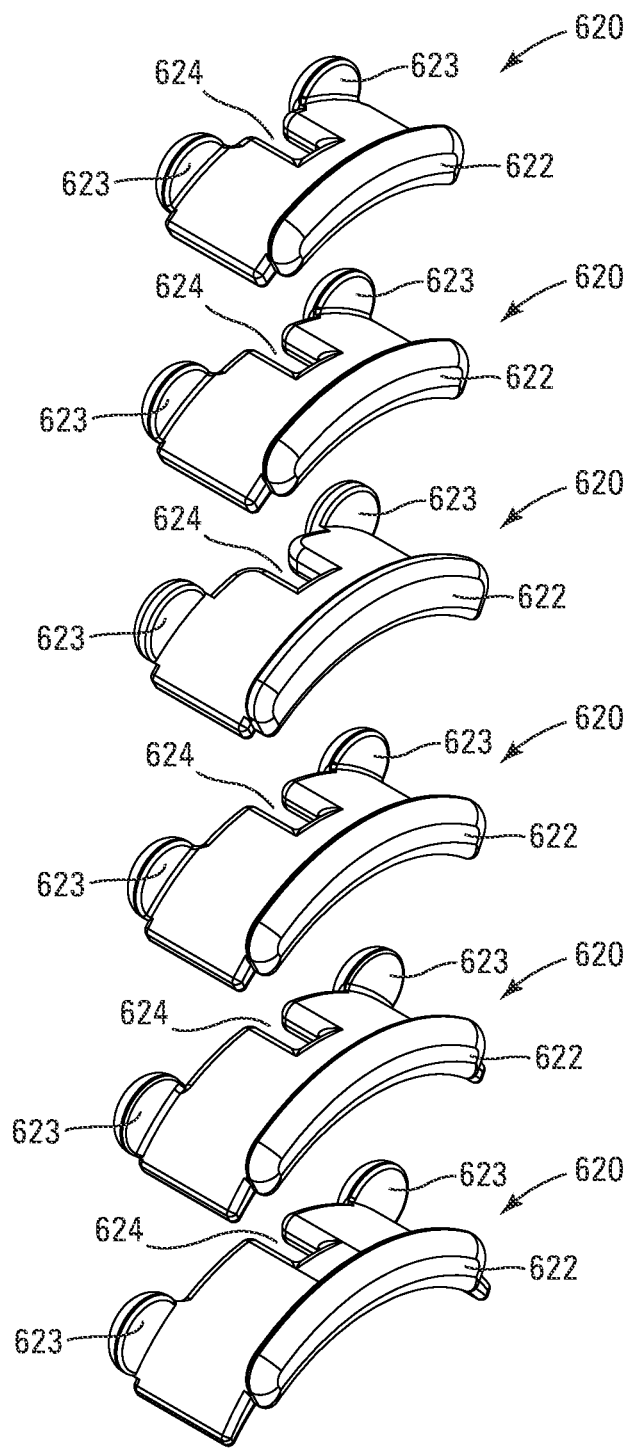
FIG. 26 is an upper perspective front view of a set of six spacers of different widths.
Figure 27:
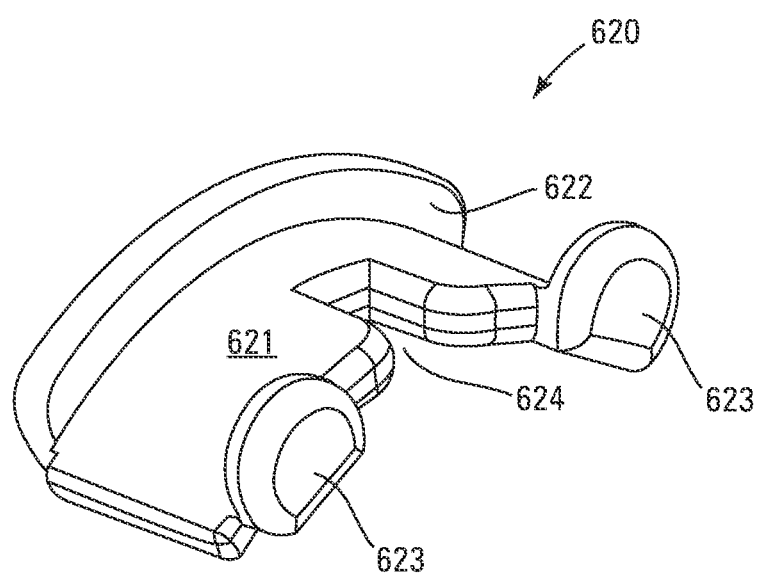
FIG. 27 is an upper perspective rear view of one of the spacers depicted in FIG. 26.

Other embodiments may incorporate rigid inelastic sections within the cylindrical annulus 110, which may be composed of, but not limited to, thermoplastics including ABS, polypropylene and nylon or thermosetting materials including phenolic and melamine, ceramics or hard elastomers, in addition to section(s) of soft elastic material. Referring generally to FIG. 13, one example of an embodiment incorporating a rigid inelastic section is a continuous loop band 110 formed from a rigid upper section body 410 and a flexible lower section 420 connected by a suitable connection mechanism 430. The ratio between the peripheral length of the rigid upper section body 410 and the peripheral length of the flexible lower section 420 can be varied.

Those skilled in the art will recognize that changes and modifications may be made in the described embodiments without departing from the nature and scope of the present invention. To the extent that such modifications and variations do not depart from the spirit of the invention, they are intended to be included within the scope thereof.

Method of Donning to Control Incontinence

The device 100 is operable for controlling male incontinence, by (i) manually radially stretching the continuous elastic compression band 110 so as to enlarge the lumen 119, (ii) inserting the penis P of a male W in need of incontinence control through the enlarged lumen 119 with the bump 120 on the device 100 positioned proximate the underside $P_2$ of the penis P, and (iii) releasing the band 110 whereby the band 110 contracts around the shaft $P_1$ of the penis P, and the bump 120 presses against and restricts the urethra U.

Expanding the sleeve 110 for application to the shaft $P_1$ of the penis P near the base can be achieved by insertion of the index finger and middle finger (not shown) of each hand (not shown) into the sleeve 110 center and pulling in opposite directions. The low modulus characteristic of the elastomer allows the unit 110 to be stretched sufficiently prior to positioning in the applied condition. The removal therefrom can be achieved by use of the respective gripping appendages 130, when stretched in opposite radial directions.

The proper unit size and/or tension for different users varies, which could be addressed by manufacturing different size devices 100. This invention partially addresses such sizing needs with its design. Users W requiring less tension can remove material from the radial ring (i.e., the radial wings 140) outside the main body 110. After the proper tension is established, no additional sizing or adjustments should be necessary.

Urinating While Wearing the Device

Removal or adjustment of the device 100 is not necessary prior to, during, or after urination, due to the flexible characteristics of the soft body construction.

A male W wearing the device 100 can urinate while wearing the device 100 by consciously initiating voiding of his bladder without adjusting or removing the device 100, whereby (i) the bladder contracts, (ii) the bladder outlet relaxes, and (iii) the flow of urine within the urethra exerts a pressure sufficient to overcome the pressure exerted upon the urethra by the bump 120 on the device 100 so as to permit micturition.

Overnight Use

When necessary or desired, the device 100 may be worn throughout the night. However, it is recommended that the device 100 be positioned forward from the base of the penis P to gain skin relief after daytime use positioned at or near the base. During daytime use, if positioned forward, performance would normally be degraded, but not so at night, due to reduced intravesical pressures when lying down.

Method of Doffing

The device 100, when equipped with removal loops 130, can be removed from operable engagement with a penis P by (i) inserting at least one finger tip from a first hand into a first removal loop 131, and inserting at least one finger tip from a second hand into the other removal loop 132, (ii) manually stretching the elastic compression band 110 so as to enlarge the lumen 119 by pulling the loops 130 away from one another, and (iii) sliding the manually stretched elastic compression band 110 off the penis P.

Alternatively, a wearer W can insert at least a first and a second finger tip from a first hand into the first removal loop 131, and inserting at least a first and a second finger tip from a second hand into the other removal loop 132, and then, in addition to manually stretching the elastic compression band 110 so as to enlarge the lumen 119 by pulling the loops 130 away from one another, expanding the first and second finger tips in each removal loop 130 away from one another.

Second Aspect

Construction

Referring to FIGS. 14-18, the male incontinence control device 600 has a body 610 formed as a single piece of silicone rubber, thermoplastic elastomer, or other elastomer. The elastomer preferably has a low durometer, possibly with a Shore A hardness of 5-15 with an elongation of at least 200%. The main body 611 is a tubular shape with an internal knob 614 on the bottom to occlude the urethra to impede/reduce urine flow.

The main tubular body 611 also has attached upper 612 and lower 613 features/loops to assist in the donning and removal of the device. The lower loop 613 is angled forward to reduce contact with the scrotum. Slightly above the main tubular body 611, near the attachment points of the upper loop 612, is a strap 615 creating a slot into which a spacer 620 can be inserted (hereinafter spacer opening). This strap 615 can alternatively be referenced as a secondary band 615 radially spaced from the main tubular body 611 with the secondary band 615 secured at its circumferentially spaced lateral end points to the main tubular body 611. Near the center of the containment strap 615 is an optional post 616 connecting the main tubular body 611 to the containment strap 615. This post 616 will keep an inserted spacer 620 centered. The post 616 can also have a gusset 617 to the main tube 611 to stiffen the tube 611 and reduce bending.

The elastomeric body 610 can have a main tube 611 that varies in length, wall thickness, and diameter (inner circumference) depending on the elastomeric material used and the user needs.

The thinner the walls of the tube 611 (with the same cross-sectional area), the less pressure is placed on the penis, reducing the restriction of blood flow to the penis.

Referring to FIGS. 19-27, the spacer 620 can be made of hard plastic or metal. It is preferably arc-shaped with a curvature similar to the main tubular body 611 of the elastomer. The main arc 621 of the spacer 620 may have a slot 624 near the center to mate with the optional post 616 connecting the main tubular body 611 and the strap 615. This slot 624 cooperates with the post 616 to keep the spacer 620 centered. The spacer 620 may come in several widths or may be adjustable in width to accommodate the needs of different users. The main arc 621 of the spacer 620 may have a raised edge on the front side 622 to aid in positioning and to keep it in position when the main body 611 is stretched to place the unit on the user. The arc 621 on the backside may have two raised edges/disks 623 on either side of the centering slot 624 in the main arc 621. These disks 623 cooperate with the front stop 622 to keep the spacer 620 centered below the strap 615 and to prevent the spacer 620 from slipping back out from under the spacer holding strap 615, during donning and doffing of the unit. The spacer 620 should not interfere with stretching the circumference of the main body 611 to apply the unit, but it should prevent the main body 611 from elastically contracting below a set diameter (interior circumference). The limited minimum circumference prevents excessive pressure on the perimeter of the penis, which could reduce blood flow and also affects the amount of pressure on the urethra by the internal knob 614 of the main body 611.

Figure 28:
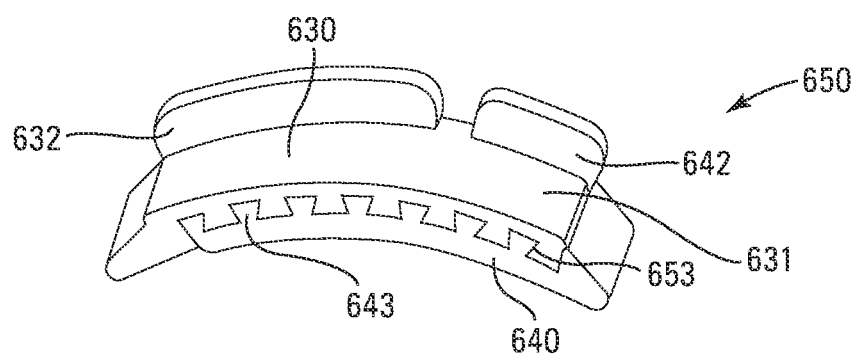
FIG. 28 is an upper perspective of a two-part adjustable width spacer in the narrowest assembly configuration in accordance with the invention.
Figure 29:
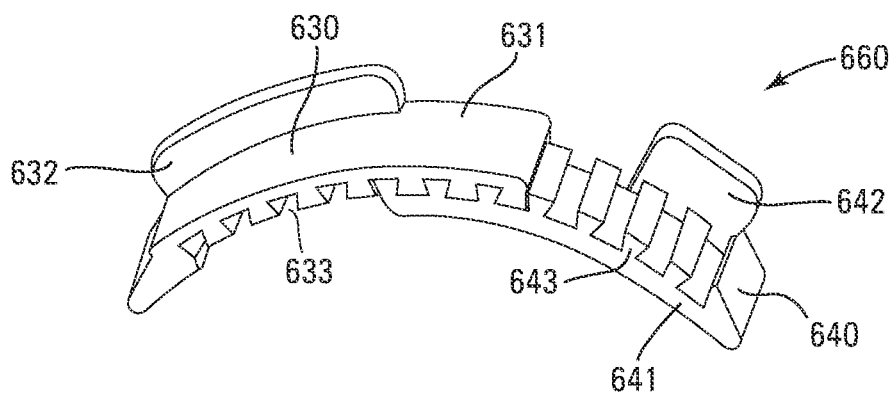
FIG. 29 is an upper perspective of the spacer depicted in FIG. 28 in a wider assembly configuration.

Referring to FIGS. 28 and 29, as an alternative to having spacers 620 of varying widths, spacers 620 of adjustable widths may be employed. FIGS. 28 and 29 illustrate one embodiment of an adjustable width spacer 620. This embodiment consists of two parts: An outer arc portion 630 that mates with an inner arc portion 640 to form a combined arc that is adjustable in length. In this version, the outer arc 630 has several receiving dovetail slots 633. The inner arc 640 has several complimentary dovetails 643 that can be inserted into the slots 633 to form a rigid assembly. Depending on which slots 633 and 643 of the outer arc 630 and the inner arc 640 respectively are mated, the overall width of the spacer 620 can be varied. FIG. 28 shows an assembly at the minimum width of this particular design. FIG. 29 shows an assembly of the same two parts, 630 and 640, with the dovetails mated, creating a wider spacer 620. In both cases, the assembly of the halves 630 and 640 creates a rigid spacer 620.

In this particular embodiment of an adjustable width spacer, there is no center slot 624. Other embodiments could have a center slot 624 and that there are many other mating features, other than the dovetails that are illustrated here, to create an adjustable width spacer 620. The embodiment shown is not intended to limit the many ways an adjustable spacer 620 can be constructed. Other variations are intended to be within the scope of this patent application.

Referring to FIGS. 14-18, the top loop 612 can be an integral part of the unit that forms the spacer opening, as shown in the figures. However, it is also possible to attach the upper loop 612 so that it is not an integral part of the unit that forms the spacer opening. The purpose of the top loop 612 is to assist in the donning and doffing of the device and, to a lesser degree, to reduce the pressure of the knob 614 on the urethra when urinating.

The bottom loop 613 is attached to the main tube 611 on each side of the urethra occluding feature/knob 614. The purpose of the bottom loop 613 is to assist in the donning and removal of the device and, to a lesser degree, to reduce the pressure of the knob 614 on the urethra when urinating, as desired. To minimize contact with the scrotum and to allow for positioning at the base of the penis, it is desirable to have a forward bias on the bottom loop 613.

The ability to adjust the circumference of the main body 611 can provide a custom fit for each individual user, important for achieving optimum performance in impeding urine flow with little or no effect on blood flow. The size and shape of the urethra compression knob 614 is likewise important for achieving optimum performance. Therefore, it is desirable to be able to adjust the size and shape of the knob 614 to obtain the best performance and comfort for individual users. There are several ways to incorporate an adjustable knob 614 into this overall design. A nonlimiting set of embodiments to achieve an adjustable knob 614 include specifically, but not exclusively, (i) a removable knob 614 that is attached to the main body 611 by a dovetail detail, (ii) a cap that is placed on the knob 614 to increase the size and shape of the knob 614, (iii) a knob 614 that has a hole and is attached to the body 611 with a pin through the hole to anchor it in place, (iv) a molded knob 614 that has a hollow center, into which different size and or shaped rigid or flexible inserts 680 can be placed to expand the knob 614 to different shapes or dimensions. There are many other ways known to those skilled in the art to attach different size and shaped knobs 614 and to expand the elastomer to different sizes and shapes. It is intended that these other methods are included by reference and within the scope of this invention.

Figure 30:
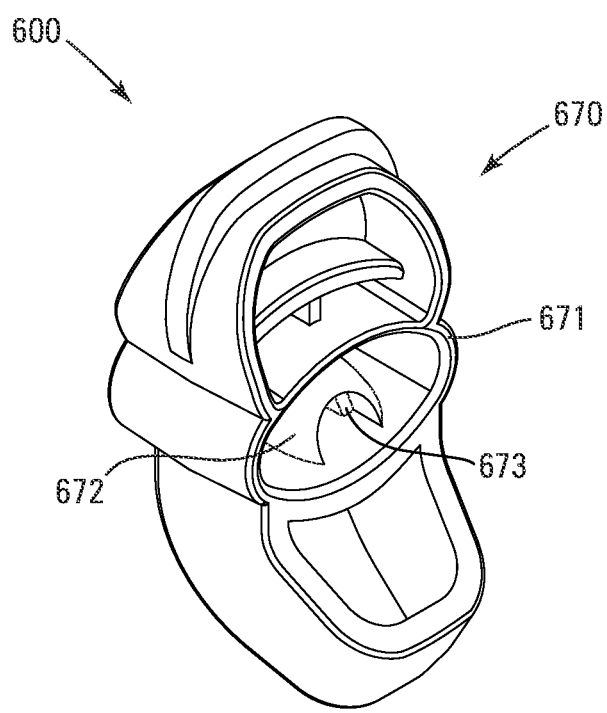
FIG. 30 is an upper perspective view of a sixth embodiment of the invention with a hole through the knob to accept an insert.
Figure 31:
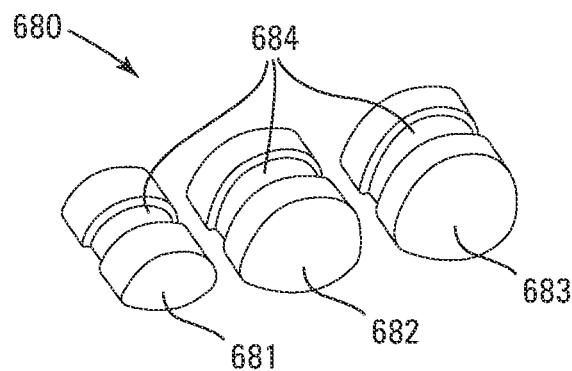
FIG. 31 is a depiction of three knob inserts of different heights compatible with the sixth embodiment of the invention depicted in FIG. 30.
Figure 32:
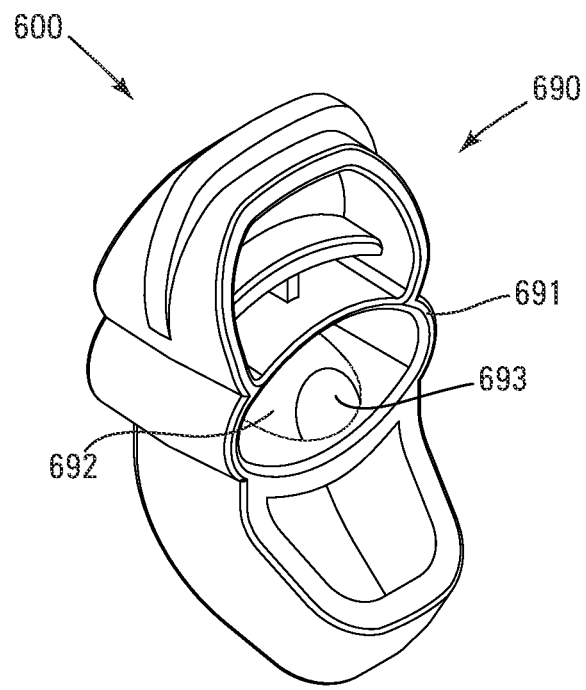
FIG. 32 is a perspective view of an assembly of the sixth embodiment of the invention depicted in FIG. 30 with the smallest of the inserts depicted in FIG. 31 installed in the hole through the knob.
Figure 33:
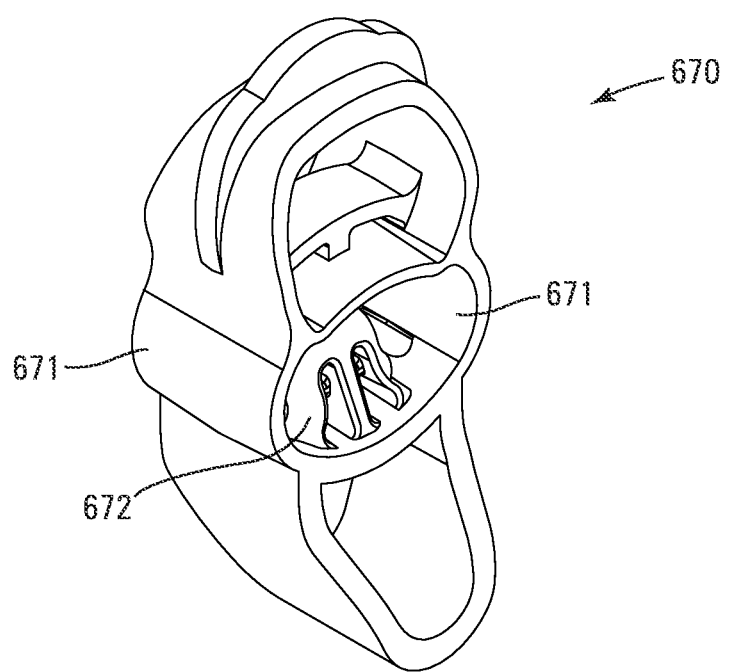
FIG. 33 is an upper perspective view of a seventh embodiment of the invention with a partially cored knob for casting purposes.

One specific example of an adjustable knob 614 is shown in FIG. 30-32. FIGS. 30 and 32 show an elastomeric body 670, 690 similar to that shown in FIGS. 14-18 with a tubular main body 671, 691, however, in this example, there is a hole through the knob 672, 692.

Within that hole is a ridge 673 to keep an insert 680 in place. Referring to FIG. 31, the insert 680 can be selected from inserts 680 of different heights and shapes. FIG. 31 shows three inserts 681, 682, 683 of the same width but different heights. Each insert 680 in this example has a groove 684 in the center that corresponds to the ridge 673 in the center of the hole through the knob 672 as depicted in FIG. 30. The groove 684 will cooperate with the ridge 673 to keep the insert 680 in place.

The taller inserts 682 and 683 will tend to stretch the knob 672, 692 and result in a taller knob 672, 692 than the shorter knob 681 that is inserted into the knob 672, 692 as shown in FIG. 32.

These inserts 680 can be of a hard material or they may be of a softer material, similar to the main body 611, to create a firmer or softer knob 672 to fit the needs of the user.

Unless otherwise defined, all technical and scientific terms used herein have the same meaning as commonly understood by one of ordinary skill in the art to which this invention belongs.

Although methods and materials similar to or equivalent to those described herein can be used in the practice or testing of this invention, suitable methods and materials are described above. All publications, patent applications, patents, and other references mentioned herein are incorporated by reference in their entirety to the extent allowed by applicable law and regulations. This invention may be embodied in other specific forms without departing from the spirit or essential attributes thereof, and it is therefore desired that the present embodiment be considered in all respects as illustrative and not restrictive. Any headings utilized within the description are for convenience only and have no legal or limiting effect.

Operation of a Preferred Embodiment

Once a spacer 620 is inserted into the elastomeric body 610, it will increase the width of the main body 611 in the area between the two legs of the upper loop 612. This will increase the overall diameter/interior-circumference of the main body 611 to a greater size from its relaxed state. The increased diameter will reduce the perimeter pressure on the penis to ensure good blood flow and comfort. The increased diameter will also reduce the pressure the knob 614 places on the urethra.

The presence of the spacer 620 will not affect the ability to increase the circumference of the main body 611 when donning and doffing the device 610.

Unless otherwise defined, all technical and scientific terms used herein have the same meaning as commonly understood by one of ordinary skill in the art to which this invention belongs.

Although methods and materials similar to or equivalent to those described herein can be used in the practice or testing of this invention with spacer, suitable methods and materials are described above. All publications, patent applications, patents, and other references mentioned herein are incorporated by reference in their entirety to the extent allowed by applicable law and regulations. This invention may be embodied in other specific forms without departing from the spirit or essential attributes thereof, and it is therefore desired that the present embodiment be considered in all respects as illustrative and not restrictive. Any headings utilized within the description are for convenience only and have no legal or limiting effect.

There has thus been outlined, rather broadly, some of the features of this invention in order that the detailed description thereof may be better understood and in order that the present contribution to the art may be better appreciated. It is to be understood that this invention is not limited in its application to the details of construction or to the arrangements of the components set forth herein or illustrated in the drawings. This invention is capable of other embodiments and of being practiced and carried out in various ways. Also, it is to be understood that the phraseology and terminology employed herein are for the purpose of the description and should not be regarded as limiting.

We claim:

1. A male incontinence control device comprising:
    (a) a tubular elastomeric primary band defining axial, radial and circumferential directions, and having a circumference configured and arranged to encircle a flaccid penis without inflicting penile ischemia,
    (b) an elastomeric secondary band radially spaced from the primary band to form a slot therebetween, the secondary band secured to the primary band at circumferentially spaced lateral end points of the secondary band,
    (c) a rigid spacer positioned within the slot, imposing persistent circumferential strain upon and thereby circumferentially expanding a segment of the primary band so as to increase the circumference of the primary band, and
    (d) a radially projecting knob on the primary band, projecting inward from the primary band for pressing against and constricting a urethra of a wearer.

2. The male incontinence control device of claim 1, wherein the secondary band is further secured to the primary band at a central attachment post circumferentially intermediate the lateral end points.

3. The male incontinence control device of claim 2, wherein the spacer has a niche configured and arranged to seat with the central attachment post for maintaining circumferential positioning of the spacer within the slot.

4. The male incontinence control device of claim 2, wherein the spacer has a selectively adjustable lateral length for imposing different levels of strain upon the segment of the primary band.

5. The male incontinence control device of claim 1, further comprising an upper loop extending radially outward from and attached to the primary band proximate the lateral end points of the secondary band, operable for use as a pull handle for positioning the male incontinence control device upon a penis.

6. The male incontinence control device of claim 5, wherein (i) the knob has circumferentially spaced sides and (ii) the device further comprises a lower loop diametrically opposed to the upper loop, the lower loop extending radially outward from and attached to the primary band proximate each side of the knob, operable for use as a pull handle for positioning the male incontinence control device upon the penis.

7. The male incontinence control device of claim 6, wherein the lower loop is formed to extend in a forward axial direction from a proximal end attached to the primary band to a distal end radially spaced from the primary band, whereby contact between the lower loop and a scrotum is reduced when the device is worn near the base of the penis.

8. The male incontinence control device of claim 1, wherein the knob is selectively replaceable with a replacement knob having a different size and/or shape.

9. The male incontinence control device of claim 1, wherein the knob is a hollow elastic bump capable of removably accepting insertion of an object selected from a set of objects of variable size.

10. The male incontinence control device of claim 1, wherein the knob is selectively attachable and detachable for customized selection of a knob from a set of knobs of variable size.

11. A male incontinence control device comprising:
    (a) a single piece low modulus elastomeric member that includes (i) a sleeve having a circumference and operable for encircling a flaccid penis without inflicting penile ischemia, and (ii) a member configured and arranged to receive a rigid spacing device,
    (b) a rigid spacing device configured and arranged for engaging the member to circumferentially expand at least a portion of the sleeve so as to increase the circumference of the sleeve when engaged, and
    (c) a radially inward projecting knob on the sleeve operable for occluding a urethra of a wearer.

12. The male incontinence control device of claim 11, wherein the rigid spacing device is selectively replaceable with a replacement spacing device having a different size and/or shape for effecting a different length of circumferential expansion of the portion of the sleeve.

13. The male incontinence control device of claim 11, wherein the rigid spacing device has a selectively adjustable dimension operable for increasing and decreasing the circumference of the sleeve when adjusted.

14. The male incontinence control device of claim 11, further comprising a removal feature attached to and extending from the sleeve operable for assisting in hand-pulled expansion of the sleeve for donning and doffing the device onto and off from a penis.

15. The male incontinence control device of claim 14, wherein the removal feature includes an upper loop extending radially outward from and attached to the sleeve.

16. The male incontinence control device of claim 15, wherein the removal feature further includes a lower loop diametrically opposed to the upper loop, the lower loop extending radially outward from and attached to the sleeve.

17. The male incontinence control device of claim 16, wherein the lower loop is formed to extend in a forward axial direction from a proximal end attached to the sleeve to a distal end radially spaced from the sleeve, whereby contact between the lower loop and a scrotum is reduced when the device is worn near the base of a penis.

18. A male incontinence control assembly, comprising:
 (a) an elastomeric element, the element including at least:
  (1) a tubular primary band defining axial, radial and circumferential directions, and having a circumference, and
  (2) a secondary band radially spaced from the primary band to form a circumferentially extending slot therebetween, the secondary band secured to the primary band at circumferentially spaced lateral end points of the secondary band,
  (3) wherein the primary band is configured and arranged to encircle a flaccid penis without inflicting penile ischemia,
 (b) a radially projecting knob extending inward from the primary band, the knob configured and arranged for pressing against and constricting a urethra of a wearer, and
 (c) a set of rigid spacers, each spacer (i) operable for selective positioning within the slot for imposing persistent circumferential strain upon and thereby expanding a segment of the primary band so as to increase the circumference of the primary band, and (ii) having a different size for imposing different levels of circumferentially expanding strain upon the segment of the primary band to effect different increases in circumferential expansion of the primary band.

19. The male incontinence control assembly of claim 18, wherein the element further includes an upper loop extending radially outward from and attached to the primary band proximate the lateral end points, operable for use as a pull handle for (i) positioning the male incontinence control device upon a penis, (ii) removing the male incontinence control device from the penis, and (iii) reducing urethral pressure when voiding a bladder.

20. The male incontinence control device of claim 19, wherein the element further includes a lower loop diametrically opposed to the upper loop, the lower loop extending radially outward from and attached to the primary band proximate each side of the radially projecting knob, operable for use as a pull handle for (i) positioning the male incontinence control device upon the penis, (ii) removing the male incontinence control device from the penis, and (iii) reducing urethral pressure when voiding the bladder.

21. A male incontinence control assembly, comprising:
 (a) an elastomeric element, the element including at least:
  (1) a tubular primary band defining axial, radial and circumferential directions, and having a circumference, and
  (2) a secondary band radially spaced from the primary band to form a circumferentially extending slot therebetween, the secondary band secured to the primary band at circumferentially spaced lateral end points of the secondary band, and
  (3) a radially inwardly projecting knob on the primary band configured and arranged for pressing against and constricting a urethra of a wearer,
  (4) wherein the primary band is configured and arranged to encircle a flaccid penis without inflicting penile ischemia, and
 (b) a set of rigid spacers, each spacer (i) operable for selective positioning within the slot for imposing persistent circumferential strain upon and thereby expanding a segment of the primary band so as to increase the circumference of the primary band, and (ii) having a different dimension for imposing different levels of circumferentially expanding strain upon the segment of the primary band to effect different increases in circumferential expansion of the primary band.

* * * * *